US007468353B2

(12) United States Patent
Bevec

(10) Patent No.: US 7,468,353 B2
(45) Date of Patent: Dec. 23, 2008

(54) BIOLOGICALLY ACTIVE SUBSTANCE OF A VASOACTIVE INTESTINAL PEPTIDE FOR TREATING INTERSTITIAL LUNG DISEASES

(75) Inventor: Dorian Bevec, Gentilino (DE)

(73) Assignee: Mondobiotech Laboratories Anstalt, Vaduz (LI)

( * ) Notice: Subject to any disclaimer, the term of this patent is extended or adjusted under 35 U.S.C. 154(b) by 0 days.

(21) Appl. No.: 10/564,849

(22) PCT Filed: Jul. 12, 2004

(86) PCT No.: PCT/CH2004/000439

§ 371 (c)(1), (2), (4) Date: Jan. 13, 2006

(87) PCT Pub. No.: WO2005/004899

PCT Pub. Date: Jan. 20, 2005

(65) Prior Publication Data

US 2006/0223748 A1 Oct. 5, 2006

(30) Foreign Application Priority Data

Jul. 14, 2003 (CH) .................................... 1229/03

(51) Int. Cl.
*A61K 38/08* (2006.01)

(52) U.S. Cl. ....................................................... 514/15

(58) Field of Classification Search ....................... None
See application file for complete search history.

(56) References Cited

U.S. PATENT DOCUMENTS

| | | | |
|---|---|---|---|
| 3,898,329 | A | 8/1975 | Said et al. |
| 4,237,046 | A | 12/1980 | Bodanszky |
| 6,322,810 | B1 | 11/2001 | Alkan-Onyuksel et al. |

FOREIGN PATENT DOCUMENTS

| | | |
|---|---|---|
| EP | 1 103 270 A1 | 5/2001 |
| WO | 01/34088 | 5/2001 |
| WO | WO 02/43746 | 6/2002 |
| WO | WO 03/045330 | 6/2003 |
| WO | WO 03/046145 | 6/2003 |

OTHER PUBLICATIONS

Todate et al. "Increased Numbers of Dendritic Cells in the Bronchiolar Tissues of Diffuse Panbronchiolitis" Am. J. Resp. Crit. Care Med., 2000, 162, 148-53.*

International Preliminary Examination Report for PCT/CH2004/000439, dated May 1, 2006.

Written Opinion of the International Searching Authority for PCT/CH2004/000439.

International Search Report, PCT/CH2004/000439, Mar. 15, 2005.

Keith I.M., The Role of Endogenous Lung Neuropeptides in Regulation of the Pulmonary Circulation, Physiological Research, vol. 49(5), pp. 519-537, 2000.

Pavlou T.A. et al., American Review of Respiratory Disease, vol. 14, p. A536 Suppl. S, 1993.

Iwanaga, et al., Vasoactive Intestinal Peptide VIP Protects Against Acid-Induced Acute Lung Injury in Isolated Perfused Rat Lungs, Japanese Journal of Thoracic Diseases, vol. 27(7) pp. 789-795 (Abstract Only) 1989.

Maruno, et al., VIP inhibits basal and histamine-stimulated proliferation of human airway smooth muscle cells, American Journal of Physiology, vol. 268(6) pp. L1047-L1051, 1995.

Kawasaki, et al., The mechanisms of the relaxation induced by vasoactive intestinal peptide in the porcine coronary artery, British Journal of Pharmacology, vol. 121(5) pp. 977-985, 1997.

Platoshyn, et al., Sustained membrane depolarization and pulmonary artery smooth muscle cell proliferation, American Journal of Physiology, vol. 279(5) pp. C1540-C1549, Nov. 1, 2000.

* cited by examiner

*Primary Examiner*—Cecilia Tsang
*Assistant Examiner*—Christina Marchetti Bradley
(74) *Attorney, Agent, or Firm*—Amin, Turocy & Calvin, LLP

(57) ABSTRACT

The invention describes for the first time the preclinical/cellular and clinical relevance of VIP, PACAP as well as of substances with the same biological activity as VIP and PACAP for the treatment of interstitial lung infections such as idiopathic pulmonary fibrosis, hypersensitive pneumonia or diffused panbronchiolitis. VIP and PACAP are synthesised in different areas of the central nervous system, e.g. in specific cerebral areas such as the hippocampus and the cortex, as well as in the peripheral ganglia. VIP is also released by immune cells.

15 Claims, No Drawings

BIOLOGICALLY ACTIVE SUBSTANCE OF A VASOACTIVE INTESTINAL PEPTIDE FOR TREATING INTERSTITIAL LUNG DISEASES

The invention relates to using biologically and pharmacologically highly active peptides for treating interstitial lung infections such as idiopathic pulmonary fibrosis (IPF), hypersensitive pneumonia or diffused panbronchiolitis. The inventive peptides used for treating said infections contain at least one type of highly conservable sprecific amino acid sequences which appear to play an important role in pathogenesis of corresponding lung infections. It is proved that known natural peptide VIP (Vasoactive Intestinal Peptide) and PACAP (Pituitary Adenylate Cyclase-Activating Polypeptide containing said sequences constitute the active substances for treating successfully idiopathic pulmonary fibrosis and hypersensitive pneumonia. Furthermore, the present invention expounds compositions which are useful for treating interstitial lung infections.

BACKGROUND OF THE INVENTION

Interstitial Pulmonary Infections

Interstitial infections are a heterogeneous group of chronic inflammation reactions in the lung. There exist different forms of interstitial lung infections, e.g. idiopathic pulmonary fibrosis (IPF), hypersensitive pneumonia or diffused panbronchiolitis. The pathophysiological processes of said diseases are characterised by a combination of tissue injuries and excessive tissue repair processes which leads normal cellular growth to progressive scarring. Said reaction is characterised by repeated destructions of tissue and an intense proteolytic activity with degradation of the structure of extracellular matrix components. Said processes modify the cellular immune response and cause highly induced proliferation of mesenchymal tissue.

Cytokines, such as the tumour necrosis factor alpha, and further growth factors such as the "Transforming growth factor beta1 (TGFbeta 1), have been associated in the art with these processes. TGFbeta appears to be the most important growth factor because it highly stimulates the growth of mesenchymal tissue and because of its capacity to modify cellular immune processes.

TGFbeta is known to cause serious lung fibrosis in animal models in case of increased production thereof. A significantly increased production of said growth factor also appears in cases of human pulmonary fibrosis. It is also known that TGFbeta has immune modifying effect, which includes inhibition of the production of Interferon gamma, suppression of immune reactions correlated to Interferon gamma and induction of immune suppressive CD8+ lymphocytes. Indeed, a modification of the cellular immunity which is not related to the original tissue injury in patients with progressive fibrosises is known for years. More recent researches proved that the progressive scarring in idiopathic pulmonary fibrosis includes modifying the cytokine balance which leads to the reaction called "helper T type 2". This reaction is characterised by increase of Th2 cytokines, such as interleukin 4 (IL-4), IL-10 and IL-13, as well as by decrease or complete loss of the Interferon gamma production, which is the principle mediator of the reaction called "helper T 1". In contrast to chronic inflammatory reactions occurring in fibrosis, an acute inflammation of the lung interstitium, e.g. as a result of bacteria infection, is characterised by simultaneous production of cytokines for the production of both type 1 helper T and type 2 helper T, such as the Interferon gamma, IL-12 and IL-4. Additionally, the production of TGFbeta increases, which indication activation of wound healing.

Earlier cellular processes of the disease can hardly be identified due to the fact that idiopathic pulmonary fibrosis is generally diagnosed in an advanced state of disease. The intensity of wound healing is directly influenced by inflammation mechanisms which cause in turn an increased metabolic rate of extracellular matrix components and other cellular components. Chronic inflammations, which are generally caused by infections, cause pathologically excessive wound healing. Even in case of knowing the agents which cause the inflammation, no medical drugs for a successful treatment of organ fibrosis do exist on the market for now. Millions of persons die due to a slow destruction of vital organ systems by a pathological restructuring of the functional tissue. This process is described by the term of fibrosis and is started and regulated by fibroproliferative mechanisms. In our day, the only solution consists in organ transplantation, which means many risks and high costs.

Fibroproliferative reactions affect all organs of the body. Concerning the gas exchange tissue of the lung, they are known under the term of pulmonary fibrosis, in case of affecting the liver, they are called cirrhosis, and in the kidney said reactions are named glomerulosclerosis. All diseases mentioned above can be described as fibroproliferative diseases. In fibrosis, intact tissue is progressively replaced by connective tissue and supporting tissue. This process is based on a pathologically accelerated increase of those tissue cells normally responsible for wound healing. Fibroproliferative diseases are therefore defined diseases with uncontrolled acceleration of wound healing. In fibrosis, the functional organ tissue is replaced until complete loss of the organ function.

Today, more than 150 different mechanisms are known to cause pulmonary injuries, which in turn can cause fibroproliferative wound healing.

Among these mechanisms are chronic infections, exposure to organic and mineral dust, medication and autoimmune mechanisms. The fibriotic process is nonetheless not correlated to said mechanisms. Minor inflammations may result in a dramatic acceleration of the fibrotic process. Chronic virus diseases are probably the most frequent causes of progressive fibrosises, in spite of immunosuppressive treatments. Similar conditions apply to chronic bacteria and fungus infection with or without gastric eructation reaction causing a chronic inflammation of the terminal bronchia which directly influences the chronic wound healing process in the adjacent alveoli. On the cellular scale, the cells presenting antigens such as the dentritic cells play an important role in the pathogenesis of said diseases. They activate in a too intense manner e.g. the T-lymphocytes, which can lead to chronic immune activation. Substances for the treatment of said diseases are therefore needed for inhibiting the excessive activity of dentritic cells.

SUMMARY OF THE INVENTION

Vasoactive Intestinal Peptide (VIP):

VIP is a peptide consisting of 28 amino acids with the following sequence (from the N- to the C-terminus):

```
His-Ser-Asp-Ala-Val-Phe-Thr-Asp-Asn- (SEQ ID NO. 1)
Tyr-Thr-Arg-Leu-Arg-Lys-Gln-Met-Ala-
Val-Lys-Lys-Tyr-Leu-Asn-Ser-Ile-
Leu-Asn.
```

Healthy persons possess a VIP concentration of approximately 40 pg/ml of serum. VIP is a prevalent neurohormone which regulates a high number of physiological effects such as gastrointestinal secretion, relaxation of the smooth gastrointestinal muscles and lipolysis in adipocytes. Under physiological conditions, VIP is a neuroendocrine mediator. Certain reports indicate the regulatory impact of VIP relating to growth and proliferation in benign as well as in malignant cells (Hultgardh et al. *Growth—inhibitory properties of vasoactive intestinal polypeptide. Regul. Pept.* 22, 267-274. 1988). The biological impacts are transmitted by specific receptors (VIP-R), which are situated on the surface of different cell types (Ishihara et al., *Functional expression and tissue distribution of a novel receptor for vasoactive intestinal polypeptide. Neuron* 8, 811-819. 1992). VIP influences the growth of malignant cells in neuroblastoma, breast cancer, lung and intestinal cancer (Moody et al., *Proc. Natl. Acad. Scid. USA,* 90, 4345, 1993) by inducing its own receptors. In certain cases, VIP induces a cell multiplication which is correlated to its dose (Wollmann et al., *Brain Res.,* 624, 339, 1993). VIP and biologically functional derivatives and analogues have a relaxing impact on smooth muscles (Maruno et al., *VIP inhibits basal and histamine-stimulated proliferation of human airway smooth muscle cells. Am. J. Physiol.* 268, L1047-L1051, 1995), they present a bronchodilating activity without strong secondary cardiovascular effects and they have effects in asthma, hypertension, impotence, ischemia and on neurological disorders such as the Alzheimer's disease (e.g. WO 9106565, EP 0536741, U.S. Pat. No. 3,880,826, EP 0204447, EP 0405242, WO 9527496, EP 0463450, EP 0613904, EP 0663406, WO 9735561, EP 0620008).

VIP receptors have been found in the trachea and bronchia epithelium. They are also expressed on macrophages which enclose capillaries, in the connective tissue of the trachea and of the bronchia, in alveolar walls and in lung veins and arteries. Peptiderg nerve fibres appear to synthesise VIP in the lung (Dey et al., Localization of VIP-immunoreactive nerves in airways and pulmonary vessels of dogs, cat, and human subjects. Cell and Tissue Research 220, 231-238. 1981; Said, S. I. Vasoactive intestinal polypeptide (VIP) in asthma. Ann. N.Y. Acad. Sci. 629, 305-318. 1991). VIP reduces the resistance in the pulmonary tissue (Hamasaki et al., *Releaxant action of VIP on cat pulmonary artery: comparison with acetylcholine, isoproterenol, and PGE*1. *J. Appl. Physiol.* 54, 1607-1611. 1983; Iwabuchi et al., *Vasoactive intestinal peptide causes nitric oxide-dependent pulmonary vasodilation in isolated rat lung. Respiration* 64, 54-58. 1997; Saga; T. and Said, S. I. *Vasoactive intestinal peptide relaxes isolated strips of human bronchus, pulmonary artery an lung parenchyma. Trans. Assoc. Am. Physicians.* 97, 304-310. 1984). Other researches show a high expression rate of VIP-R in the lungs characterised by a high absorption rate of radioactively marked VIP (Rader et al., 123I-*labelled vasoactive intestinal peptide receptor scintigraphy in patients with colorectal cancer. Br. J. Cancer* 78, 1-5. 1998; Raderer et al., *Iodine*-123-*vasoactive intestinal peptide receptor scanning in patients with pancreatic cancer. J. Nucl. Med.* 39, 1570. 1998; Raderer et al., *Value of peptide receptor scintigraphy using* (123)*I-vasoactive intestinal peptide and* (111)*In-DTPA-D-Phel-octreotide in* 194 *carcinoid patients: Vienna University Experience,* 1993 *to* 1998. *J. Clin. Oncol.* 18, 1331-1336. 2000; Virgolini et al., *Vasoactive intestinal peptide receptor scintigraphy. J. Nucl. Med.* 36, 1732-1739. 1995).

Pituitary Adenylate Cyclase-Activating Polypeptide (PACAP):

PACAP is a neuropeptide consisting of 38 amino acids with the following amino acid sequence (from the N- to the C-terminus):

```
His-Ser-Asp-Gly-Ile-Phe-Thr-Asp-Ser- (SEQ ID NO. 2)
Tyr-Ser-Arg-Tyr-Arg-Lys-Gln-Met-Ala-
Val-Lys-Lys-Tyr-Leu-Ala-Ala-Val-Leu-
Gly-Lys-Arg-Tyr-Lys-Gln-Arg-Val-Lys-
Asn-Lys.
```

Two forms of the peptide have been identified: PACAP-38 and PACAP-27 which is shortened at the C-terminus. PACAP-27, which presents a 68% homology to the VIP, has the following amino acid sequence (from the N- to the C-terminus):

```
His-Ser-Asp-Gly-Ile-Phe-Thr-Asp-Ser- (SEQ ID NO. 3)
Tyr-Ser-Arg-Tyr-Arg-Lys-Gln-Met-Ala-
Val-Lys-Lys-Tyr-Leu-Ala-Ala-Val-Leu.
```

PACAP is a strong stimulator of adenylate cyclase and thus induces 3,5-cyclic adenosine monophosphate (cAMP) in different cell types. The agent acts, as an hormone of the hypothalamus, as a neurotransmitter, as a neuromodulator, a vasodilator and as a neurotrophic factor. PACAP also stimulates the release of insulin. As a neurotrophic factor, PACAP contributes to cerebral development during the embryogenesis. In the fully developed brain, PACAP appears to act as a neuroprotective factor which prevents neuronal degradation by multiple injuries. PACAP is frequent in cerebral and peripheral organs, in particular in the pancreas, the gonads and the respiratory tract. Three PACAP receptors are described. The receptor type I has high affinity for PACAP (and very low affinity for VIP), whereas the affinity of receptor type II is similar for PACAP and VIP. It exists another PACAP specific receptor PAC1.

In the present invention, we describe the use of known agents appropriate for the synthesis of drugs for the prevention and/or treatment of interstitial lung disorders, such as e.g. idiopathic pulmonary fibrosis, hypersensitive pneumonia or diffused panbronchiolitis.

Surprisingly, it was found out that peptides with the highly conservated decapeptide amino acid sequence Arg-Lys-Gln-Met-Ala-Val-Lys-Lys-Tyr-Leu (SEQ ID NO. 4)

are highly effective inhibitors of the maturation of dentritic cells and that they are highly effective when given to patients who suffer from idiopathic pulmonary fibrosis, hypersensitive pneumonitis or diffused panbronchiolitis. It is preferable to use substances containing said amino acid sequence and in all 10-60, preferably 10-38, most preferably 10-28 or 10-27 amino acids and possessing the same properties as VIP and PACAP, which also contain the said amino acid sequence.

In general, we found out that peptides and polypeptides similar to VIP and PACAP with the above-mentioned therapeutical function and efficiency contain the following amino acid sequence:

$(A)_n$-Arg-Lys-Gln-Met-Ala-Val-Lys-Lys-Tyr-Leu-$(B)_m$ wherein A, B represent any natural amino acid and A and B are independent of each other; n, m replacing values from 0-25; n and m are independent of each other. The value of is preferably 4-18, more preferably 5-15 and most preferably 10-15.

Polypeptides or peptides, wherein $(A)_n$ (if n>2) includes the tripeptide sequence His-Ser-Asp (SEQ ID NO. 14) and/or Phe-Thr-Asp (SEQ ID NO. 13) in direction of the N-terminus of the decapeptide sequence specified above (1-10 amino acids), possess an increased activity.

Polypeptides have a particularly improved activity with $(A)_n$ (if n>2) being $(X)_0$-Phe-Thr-Asp-$(Y)_p$ and $(X)_o$ (if o>2) being $(X')_q$-His-Ser-Asp-$(X'')_r$; X, Y, X', X" being natural amino acids; o, p can take values from 0-11, r, q can take values from 0-4. Values of o and p from 0-8 are preferable, more preferable values from 1-5. Preferable values of r are 0-2.

Preferable examples of the described generic formula possess the following amino acid sequences

```
His-Ser-Asp-Ala-Val-Phe-    (VIP, SEQ ID NO. 1)
Thr-Asp-Asn-Tyr-Thr-Arg-
Leu-Arg-Lys-Gln-Met-Ala-
Val-Lys-Lys-Tyr-Leu-Asn-
Ser-Ile-Leu-Asn

His-Ser-Asp-Gly-Ile-Phe-    (PACAP-38, SEQ ID NO. 2)
Thr-Asp-Ser-Tyr-Ser-Arg-
Tyr-Arg-Lys-Gln-Met-Ala-
Val-Lys-Lys-Tyr-Leu-Ala-
Ala-Val-Leu-Gly-Lys-Arg-
Tyr-Lys-Gln-Arg-Val-Lys-
Asn-Lys

His-Ser-Asp-Gly-Ile-Phe-    (PACAP-27, SEQ ID NO. 3)
Thr-Asp-Ser-Tyr-Ser-Arg-
Tyr-Arg-Lys-Gln-Met-Ala-
Val-Lys-Lys-Tyr-Leu-Ala-
Ala-Val-Leu
```

In summary, the present invention relates to the following object:

Use of a substance for the synthesis of drugs for treating interstitial lung disorders such as idiopathic pulmonary fibrosis or hypersensitive pneumonia and the application of said drugs in patients, said substance possessing the bioactivity of VIP or PACAP.

DETAILED DESCRIPTION OF THE INVENTION

Appropriate substances having the therapeutic effect according to the invention are substances with the same biological activity as VIP or PACAP as well as higher or lower bioactivity than named peptide and polypeptide. According to the invention, substances with same or higher bioactivity are preferable. All substances which count among this group, contain the amino acid sequence Arg-Lys-Gln-Met-Ala-Val-Lys-Lys-Tyr-Leu (SEQ ID NO. 4).

The invention also relates to derivatives of the issued peptides and polypeptides with the same biological activity.

"Same biological activity" as used herein refers to biological, physiological or therapeutic activity of functionality in comparison with the relevant properties of named peptides and polypeptides, preferably with those of VIP or PACAP.

"Derivative" as used herein refers to a peptide substance which is more or less directly derived from the corresponding peptide such as VIP or PACAP and which are modified by additions, deletions, mutations or modifications without modifying the biological properties of the original peptides. Applicable derivatives of VIP are e.g. issued in WO 8905857, WO 9106565, EP 0663406 and WO 9729126 (Fmoc protected VIP). The term also relates to conjugates of named peptides and polypeptides according to the invention which consist of the original peptide or polypeptide and which are coupled to lipophilic substances such as liposomes. VIP-liposomes are issued e.g. in WO 9527496 or WO 9735561 and possess improved properties concerning bioavailability and protection against proteolysis. Additionally, the term relates to fragments and modified fragments such as shortened fragments.

"Analogue" as used herein refers to a substance whose structure or composition is different from the peptides or polypeptides of the invention, preferably different from VIP, but without modification of the biological properties. VIP analogues can be natural or synthetic peptides as well as non-peptides. According to the invention, VIP analogues are peptides. Examples of issued VIP analogues are EP 0325044 (cyclic peptides), EP 0225020 (linear peptides), EP 0536741 (cyclic VIP modifications), EP 0405242, EP 0184309 and EP 0613904. The term also refers to VIP or PACAP homologues other than VIP or PACAP but with a structure similar to VIP. According to the invention, PACAP itself as well as its shortened form PACAP-27 can be qualified as such homologues. Preferable VIP/PACAP homologues are peptides which contain one ore more consensus amino acid sequences. Examples of named peptides are the histidine isoleucine peptide, the histidine methionine peptide, the "human growth releasing factor" (GRF), PACAP, secretin and glucagon.

"Stabilised form" as used herein refers to a derivative or an analogue, the original peptide having been modified for obtaining both increased stability and increased half-life in blood and serum. Said stabilised forms are preferable in case of the peptide being fragmented by enzymatic activity. Possible stabilised forms are cyclic peptides or polypeptides such as cyclic VIP or cyclic PACAP, fusion proteins, preferably Fc-fusion proteins or pegylated polypeptides such as pegylated VIP or PACAP. Methods for synthesising such polypeptides are known in the art. Polypeptides and proteins can be protected against proteolysis by addition of chemical groups. Such additions can prevent the proteolytic enzymes from getting into physical contact with the protein structure and thus prevent degradation. Polyethylene glycol is one such structure which has been shown to protect against proteolysis (Sada et al., J. Fermentation Bioengineering 71: 137-139, 1991). In addition to protection against proteolytic cleavage, it is known that chemical modifications of biologically active proteins have been found to provide additional advantages under certain circumstances, such as increase of stability and circulation time or decrease of immunogenicity. (U.S. Pat. No. 4,179,337; Abuchowski et al., *Enzymes as drugs.;* J. S. Holcerberg and J. Roberts, eds. pp. 367-383, 1981; Francis, *Focus on Growth Factors* 3: 4-10; EP 0 401 384)

"Fusion protein" as used herein refers to a substance which consists, in particular in its stabilised form, of a polypeptide which is according to the invention preferably VIP or a VIP derivative or analogue, such as PACAP, and which is added to a further peptide or protein. Such protein is preferably an immune globulin molecule, more preferably a fragment of it, most preferably an Fc portion of an IgG molecule, preferably an IgG1 molecule. An Fc and VIP fusion protein is issued in WO 200024278 and provides improved half-life in blood and serum. Fc-PACAP and Fc-PACAP-27 could be cited as further examples.

The substance according to the invention can be used to synthesise a drug or a diagnostic procedure for the evaluation of pathological properties in an individual.

"Individual" as used herein refers preferably to mammals, in particular humans. The substance is used in pharmaceutical compositions and formulations comprising, as a rule, pharmaceutically acceptable carriers or solvents. Methods for both the formulation and application of the substances described in the present invention can be found in "Remington's Pharmaceutical Sciences", Mack Publishing Co., Easton Pa.

"Pharmaceutically acceptable support medium" as used herein refers to an inert, non-toxic solid or liquid filler.

For inhalation, the substance should preferably be available as an aerosol. Aerosols and methods for the synthesis thereof are described in the art. Aerosols which are to be administered with inhalation appliances and which contain a peptide or polypeptide of the present invention, e.g. VIP or PACAP are preferable in case that direct treatment of pulmonary symptoms is necessary.

Unit doses according to the invention may contain daily required amounts of the substance or sub-multiples thereof to make up the desired dose.

Combination Therapy

The compounds of the invention may be administered to a patient either in the form of a single substance or in combination with further agents such as calcium channel blocking agents (diltiazem), immunosuppressive substances (prednisolone), anti-microbial agents such as antibiotics or bacteriophages which are specifically effective against either staphylococci, pseudomonads, burkholderia, haemophilus, streptococcus or other bacteria in the lungs, beta-adrenergic receptor-blocking substances and angiotensine receptor antagonists or angiotensine-converting-enzyme-inhibitors (ramipril), antiproliferative substances (atorvastatin), endotheline receptor antagonists (Bosentan, Altrasentan, Sitaxsentan, Enrasentan, BMS 193884, Darusentan, TBC 3711, BSF 208075, BSF 302146, SPP 301), or other antiproliferative substances (D-24851, Imatinib mesylate). The present invention relates as well to combination therapy of the issued peptides with at least one of the above-mentioned drugs.

Surprisingly, it was found out that the peptides and polypeptides with in particular VIP and PACAP, as it is defined above in the patent claims, are inhibitors of the maturation of human dentritic cells and have beneficial effects in the treatment of patients who suffer from idiopathic pulmonary fibrosis, hypersensitive pneumonitis or diffused panbronchiolitis.

EXAMPLE

FIGS. 1-11 show the effect of VIP on the maturation of human dentritic cells. CD 38 is a characteristic surface protein on mature dentritic cells. Low rates of said protein indicate non-maturation of cells and thus, the inability to execute their biological function. The application of 1 μmol VIP (FIG. 5), or in particular the application of 9.1 μmol VIP (FIG. 9) causes dramatic reduction of CD 83 surface molecules. Said reduction is indicated by the value M1 38.22—when measuring after application of 9.1 μmol—and compared to the value M1 81.26 (FIG. 10) of untreated cells (FIG. 1)—in the fluorescence-activated cell analysis. This procedure consists of searching the cell surfaces with the help of fluorescence-marked antibodies for the corresponding antigens (here: CD 83). The effect of VIP on the CD 83 molecule is specific because other surface molecules such as the so-called MHC I (see FIGS. 2, 6 and 10) or MHC II (see FIGS. 3, 7 and 11) are far less inhibited when treated with the same dose of VIP. This is proved by the value M1 70.57 for MHC 1 for 9.1 μmol VIP in comparison to the value M1 85.59 for MHC for untreated cells as well as by the value M1 77.73 for MHC II for 9.1 μmol VIP in comparison to the value M1 83.94 for MHC II for untreated cells.

TABLES

Untreated cells:
CD 83
FIG. 1

| Marker | % Gated | Mean |
|---|---|---|
| All | 100.00 | 202.43 |
| M1 | 81.26 | 238.31 |

MHC I
FIG. 2

| Marker | % Gated | Mean |
|---|---|---|
| All | 100.00 | 352.27 |
| M1 | 85.59 | 398.25 |

MHC II
FIG. 3

| Marker | % Gated | Mean |
|---|---|---|
| All | 100.00 | 290.14 |
| M1 | 83.94 | 335.90 |

VIP (1 μM):
CD 83
FIG. 6

| Marker | % Gated | Mean |
|---|---|---|
| All | 100.00 | 108.13 |
| M1 | 69.70 | 137.30 |

MHC I
FIG. 7

| Marker | % Gated | Mean |
|---|---|---|
| All | 100.00 | 200.61 |
| M1 | 78.69 | 242.97 |

MHC II
FIG. 8

| Marker | % Gated | Mean |
|---|---|---|
| All | 100.00 | 170.33 |
| M1 | 77.41 | 207.21 |

VIP (9.1 μM):
CD 83
FIG. 10

| Marker | % Gated | Mean |
| --- | --- | --- |
| All | 100.00 | 76.48 |
| M1 | 38.22 | 143.06 |

MHC 1
FIG. 11

| Marker | % Gated | Mean |
| --- | --- | --- |
| All | 100.00 | 136.67 |
| M1 | 70.57 | 174.61 |

MHC II
FIG. 12

| Marker | % Gated | Mean |
| --- | --- | --- |
| All | 100.00 | 175.73 |
| M1 | 77.73 | 213.25 |

USED ABBREVIATIONS

VIP=Vasoactive Intestinal Peptide
PACAP=Pituitary adenylate cyclase-activating polypeptid
IPF=idiopathic pulmonary fibrosis
TGFbeta=Transforming growth factor beta1
cAMP=3,5 cyclic adenosine monophosphate
PHI=peptide histidine isoleucine
PHM=peptid histidine methionine
GRF=peptide "human growth releasing factor"
CD 83=Cluster of Differentiation number 83
MHC I=Major Histocompatibility Complex class 1 antigen
MHC II=Major Histocompatibility Complex class 2 antigen

The invention claimed is:

1. A method for inhibiting maturation of dendritic cells for the treatment of a pulmonary disease selected from idiopathic pulmonary fibrosis, hypersensitive pneumonia or diffused panbronchiolitis, comprising administering to a patient in need thereof a peptide or a polypeptide comprising the following amino acid sequence:

Arg-Lys-Gln-Met-Ala-Val-Lys-Lys-Tyr-Leu (SEQ ID NO: 4).

2. The method according to claim 1, wherein said peptide or polypeptide further comprises at least one of the following amino acid sequences:

His-Ser-Asp (SEQ ID NO: 14); and Phe-Thr-Asp (SEQ ID NO: 13).

3. The method according to claim 1, wherein said peptide or polypeptide has the following amino acid sequence:

$(A)_n$-Arg-Lys-Gln-Met-Ala-Val-Lys-Lys-Tyr-Leu (SEQ ID NO: 4)-$(B)_m$ wherein $(A)_n$ and $(B)_m$ independently are primary amino acid sequences comprising any sequence of natural occurring amino acids;

wherein n has a value from 0 to 25 and n is the number of amino acid residues in said primary amino acid sequence $(A)_n$; and wherein m has a value from 0 to 25 and m is the number of amino acid residues in said primary amino acid sequence $(B)_m$.

4. The method according to claim 3, wherein if n>2, said primary amino acid sequence $(A)_n$ is a primary amino acid sequence:

$(X)_o$-Phe-Thr-Asp-$(Y)_p$;

wherein $(X)_o$ and $(Y)_p$ independently are primary amino acid sequences comprising any sequence of natural occurring amino acids;

wherein o has a value from 0 to 11 and o is the number of amino acid residues in said primary amino acid sequence $(X)_o$; and wherein p has a value from 0 to 11 and p is the number of amino acid residues in said primary amino acid sequence $(Y)_p$.

5. The method according to claim 4, wherein if o>2, said primary amino acid sequence $(X)_o$ is a primary amino acid sequence:

$(X')_q$-His-Ser-Asp-$(X'')_r$.

wherein $(X')_q$ and $(X'')_r$ independently are primary amino acid sequences comprising any sequence of natural occurring amino acids;

wherein q has a value from 0 to 4 and q is the number of amino acid residues in said primary amino acid sequence $(X')_q$; and wherein r has a value from 0 to 4 and r is the number of amino acid residues in said primary amino acid sequence $(X'')_r$.

6. The method according to claim 3, wherein the sequence of said peptide or polypeptide is selected from the following group:

(i) Arg-Lys-Gln-Met-Ala-Val-Lys-Lys-Tyr-Leu (SEQ ID NO: 4);

(ii) Phe-Thr-Asp-$X^1$-$X^2$-$X^3$-$X^4$-$X^5$-Arg-Lys-Gln-Met-Ala-Val-Lys-Lys-Tyr-Leu-Asn-Ser-Ile-Leu-Asn (SEQ ID NO: 5);

(iii) Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO: 6);

(iv) Phe-Thr-Asp-Ser-Tyr-Ser-Arg-Tyr-Arg-Lys-Gln-Met-Ala-Val-Lys-Lys-Tyr-Leu (SEQ ID NO:7);

(v) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu (SEQ ID NO: 9);

(vi) His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu (SEQ ID NO: 10);

(vii) His-Ser-Asp-$X^1$-$X^2$-Phe-Thr-Asp-Asp-$X^3$-$X^4$-$X^5$-$X^6$-$X^7$-Arg-Lys-Gln-Met-Ala-Val-Lys-Lys-Tyr-Leu-$X^8$-$X^9$-$X^{10}$-$X^{11}$-$X^{12}$ (SEQ ID NO: 11);

(viii) His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (VIP, SEQ ID NO: 1);

(ix) His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys (PACAP-38) (SEQ ID NO: 2);

(x) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$-$X^{21}$-$X^{22}$ (SEQ ID NO: 12); and (xi) His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu (PACAP-27, SEQ ID NO: 3); and wherein $X^1$-$X^{22}$ are any naturally occurring amino acid residue.

7. The method according to claim 1, wherein said disease is idiopathic pulmonary fibrosis.

8. The method according to claim 1, wherein said disease is hypersensitive pneumonia.

9. The method according to claim 1, wherein said disease is diffused panbronchiolitis.

10. The method according to claim 1, wherein the therapeutically effective peptides are administered as aerosols.

11. The method according to claim 2, wherein said disease is idiopathic pulmonary fibrosis.

12. The method according to claim 2, wherein said disease is hypersensitive pneumonia.

13. The method according to claim 2, wherein the therapeutically effective peptides are administered as aerosols.

14. The method according to claim 3, wherein said disease is diffused panbronchiolitis.

15. The method according to claim 3, wherein the therapeutically effective peptides are administered as aerosols.

* * * * *

```
                              SEQUENCE LISTING

<160> NUMBER OF SEQ ID NOS: 14

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25


<210> SEQ ID NO 2
<211> LENGTH: 38
<212> TYPE: PRT
<213> ORGANISM: Homo sapiens

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35


<210> SEQ ID NO 3
<211> LENGTH: 27
<212> TYPE: PRT
<213> ORGANISM: Homo sapiens

<400> SEQUENCE: 3
```

```
His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25


<210> SEQ ID NO 4
<211> LENGTH: 10
<212> TYPE: PRT
<213> ORGANISM: Homo sapiens

<400> SEQUENCE: 4

Arg Lys Gln Met Ala Val Lys Lys Tyr Leu
1               5                   10


<210> SEQ ID NO 5
<211> LENGTH: 23
<212> TYPE: PRT
<213> ORGANISM: Homo sapiens
<220> FEATURE:
<221> NAME/KEY: MISC_FEATURE
<222> LOCATION: (4)..(8)
<223> OTHER INFORMATION: X is any naturally occurring amino acid residue

<400> SEQUENCE: 5

Phe Thr Asp Xaa Xaa Xaa Xaa Xaa Arg Lys Gln Met Ala Val Lys Lys
1               5                   10                  15

Tyr Leu Asn Ser Ile Leu Asn
            20


<210> SEQ ID NO 6
<211> LENGTH: 23
<212> TYPE: PRT
<213> ORGANISM: Homo sapiens

<400> SEQUENCE: 6

Phe Thr Asp Asn Tyr Thr Arg Leu Arg Lys Gln Met Ala Val Lys Lys
1               5                   10                  15

Tyr Leu Asn Ser Ile Leu Asn
            20


<210> SEQ ID NO 7
<211> LENGTH: 18
<212> TYPE: PRT
<213> ORGANISM: Homo sapiens

<400> SEQUENCE: 7

Phe Thr Asp Ser Tyr Ser Arg Tyr Arg Lys Gln Met Ala Val Lys Lys
1               5                   10                  15

Tyr Leu


<210> SEQ ID NO 8
<211> LENGTH: 23
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: X is any naturally occurring amino acid residue
<220> FEATURE:
<221> NAME/KEY: MISC_FEATURE
<222> LOCATION: (9)..(13)
<223> OTHER INFORMATION: X is any naturally occurring amino acid residue

<400> SEQUENCE: 8
```

-continued

```
His Ser Asp Xaa Xaa Phe Thr Asp Xaa Xaa Xaa Xaa Xaa Arg Lys Gln
1               5                   10                  15

Met Ala Val Lys Lys Tyr Leu
            20


<210> SEQ ID NO 9
<211> LENGTH: 23
<212> TYPE: PRT
<213> ORGANISM: Homo sapiens

<400> SEQUENCE: 9

His Ser Asp Ala Val Phe Thr Asp Asn Tyr Thr Arg Leu Arg Lys Gln
1               5                   10                  15

Met Ala Val Lys Lys Tyr Leu
            20


<210> SEQ ID NO 10
<211> LENGTH: 23
<212> TYPE: PRT
<213> ORGANISM: Homo sapiens

<400> SEQUENCE: 10

His Ser Asp Gly Ile Phe Thr Asp Ser Tyr Ser Arg Tyr Arg Lys Gln
1               5                   10                  15

Met Ala Val Lys Lys Tyr Leu
            20


<210> SEQ ID NO 11
<211> LENGTH: 28
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: X is any naturally occurring amino acid residue
<220> FEATURE:
<221> NAME/KEY: MISC_FEATURE
<222> LOCATION: (9)..(13)
<223> OTHER INFORMATION: X is any naturally occurring amino acid residue
<220> FEATURE:
<221> NAME/KEY: MISC_FEATURE
<222> LOCATION: (24)..(28)
<223> OTHER INFORMATION: X at positions 24 - 27 may be any naturally
      occurring amino acid residue: X at position 28 may be any
      naturally occurring amino acid residue

<400> SEQUENCE: 11

His Ser Asp Xaa Xaa Phe Thr Asp Xaa Xaa Xaa Xaa Xaa Arg Lys Gln
1               5                   10                  15

Met Ala Val Lys Lys Tyr Leu Xaa Xaa Xaa Xaa Xaa
            20                  25


<210> SEQ ID NO 12
<211> LENGTH: 38
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: X is any naturally occurring amino acid residue
<220> FEATURE:
<221> NAME/KEY: MISC_FEATURE
<222> LOCATION: (9)..(13)
<223> OTHER INFORMATION: X is any naturally occurring amino acid residue
<220> FEATURE:
<221> NAME/KEY: MISC_FEATURE
<222> LOCATION: (24)..(38)
<223> OTHER INFORMATION: X is any naturally occurring amino acid residue
```

-continued

```
<400> SEQUENCE: 12

His Ser Asp Xaa Xaa Phe Thr Asp Xaa Xaa Xaa Xaa Xaa Arg Lys Gln
1               5                   10                  15

Met Ala Val Lys Lys Tyr Leu Xaa Xaa Xaa Xaa Xaa Xaa Xaa Xaa Xaa
            20                  25                  30

Xaa Xaa Xaa Xaa Xaa Xaa
        35


<210> SEQ ID NO 13
<211> LENGTH: 3
<212> TYPE: PRT
<213> ORGANISM: Homo sapiens

<400> SEQUENCE: 13

Phe Thr Asp
1


<210> SEQ ID NO 14
<211> LENGTH: 3
<212> TYPE: PRT
<213> ORGANISM: Homo sapiens

<400> SEQUENCE: 14

His Ser Asp
1
```